US008246167B2

(12) United States Patent
Legerton et al.

(10) Patent No.: US 8,246,167 B2
(45) Date of Patent: Aug. 21, 2012

(54) SYSTEMS AND METHODS FOR THE REGULATION OF EMERGING MYOPIA

(75) Inventors: Jerome A. Legerton, San Diego, CA (US); William E. Meyers, Scottsdale, AZ (US)

(73) Assignee: CRT Technology, Inc., Mesa, AZ (US)

( * ) Notice: Subject to any disclaimer, the term of this patent is extended or adjusted under 35 U.S.C. 154(b) by 282 days.

(21) Appl. No.: 12/640,121

(22) Filed: Dec. 17, 2009

(65) Prior Publication Data
US 2011/0153012 A1  Jun. 23, 2011

(51) Int. Cl.
*G02C 7/04* (2006.01)
(52) U.S. Cl. ......... 351/159.23; 351/159.18; 351/159.78; 351/159.79
(58) Field of Classification Search ............... 351/160 R, 351/160 H, 161, 162, 177, 159.18, 159.23, 351/159.78, 159.79
See application file for complete search history.

(56) References Cited

U.S. PATENT DOCUMENTS

| 1,918,848 | A | 7/1933 | Land et al. |
|---|---|---|---|
| 1,963,496 | A | 6/1934 | Land |
| 2,005,426 | A | 6/1935 | Land |
| 2,123,901 | A | 7/1938 | Land |
| 5,073,021 | A | 12/1991 | Marron |
| 5,142,411 | A | 8/1992 | Fiala |
| 5,410,375 | A | 4/1995 | Fiala |
| 5,570,143 | A | 10/1996 | Newman |
| 5,629,055 | A | 5/1997 | Revol et al. |
| 5,963,297 | A | 10/1999 | Reim |
| 6,176,579 | B1 | 1/2001 | Mandell |
| 6,217,171 | B1 | 4/2001 | Auten et al. |
| 7,025,460 | B2 | 4/2006 | Smitth et al. |
| 7,216,974 | B2 | 5/2007 | Meyers et al. |
| 7,401,922 | B2 | 7/2008 | Legerton |
| 7,503,655 | B2 | 3/2009 | Smith, III et al. |
| 2003/0086055 | A1 | 5/2003 | Morris et al. |
| 2004/0223116 | A1 | 11/2004 | Baugh |
| 2004/0232394 | A1 | 11/2004 | Khan et al. |
| 2005/0105047 | A1 | 5/2005 | Smith, III et al. |
| 2006/0203189 | A1 | 9/2006 | Ho et al. |

(Continued)

FOREIGN PATENT DOCUMENTS
EP  1394575  3/2004
(Continued)

OTHER PUBLICATIONS

International Search Report and the Written Opinion for International Application No. PCT/2010/060780 dated Feb. 15, 2011.

(Continued)

*Primary Examiner* — Scott J Sugarman
(74) *Attorney, Agent, or Firm* — Snell & Wilmer L.L.P.

(57) ABSTRACT

In accordance with exemplary embodiments of the present invention, an eye is presented with a therapeutic optical structure (e.g., corneal reshaping or by way of a contact lens) that focuses the peripheral image field in at least one meridian in front of the mid peripheral retina. In general, the therapeutic optical structure places the peripheral image field with reference to the retina in the direction and amplitude that growth is needed in order that the emerging myopia would be regulated. In accordance with exemplary embodiments of the present invention, an eye is presented with a therapeutic optical structure that further produces a central retinal image that is focused on the central retina in at least one meridian so as to not reshape the central cornea.

7 Claims, 4 Drawing Sheets

U.S. PATENT DOCUMENTS

| | | |
|---|---|---|
| 2007/0115431 A1 | 5/2007 | Smith, III et al. |
| 2007/0159601 A1 | 7/2007 | Ho et al. |
| 2007/0296916 A1 | 12/2007 | Holden et al. |
| 2008/0218687 A1 | 9/2008 | Phillips |
| 2009/0268154 A1 | 10/2009 | Meyers et al. |
| 2010/0245759 A1 | 9/2010 | Legerton et al. |
| 2010/0271589 A1 | 10/2010 | Legerton et al. |
| 2011/0085129 A1 | 4/2011 | Legerton et al. |

FOREIGN PATENT DOCUMENTS

| | | |
|---|---|---|
| WO | 9427169 | 11/1994 |
| WO | 0144838 | 6/2001 |
| WO | 2007041796 | 4/2007 |
| WO | 2008014544 | 2/2008 |
| WO | 2008131479 | 11/2008 |

OTHER PUBLICATIONS

Hecht, Eugene. Optics. Reading, MA: Addison-Wesley, 1998. pp. 360-361.

Fowles, Grant R. Introduction to Modern Optics. New York: Dover Publications, 1989. p. 180-183.

Rothmayer et al. "Irregular spin angular momentum transfer from light to small birefringent particles." Physical Review A, vol. 80 No. 4, Oct. 1, 2009, p. 6.

SYSTEMS AND METHODS FOR THE REGULATION OF EMERGING MYOPIA

FIELD OF INVENTION

The present invention relates to systems and methods for the regulation of emerging myopia.

BACKGROUND OF THE INVENTION

Animal studies have demonstrated the ability to influence the development of refractive error by placing the peripheral image field in front of or behind the retina while the central image field is accurately focused. Corneal reshaping to reduce the amplitude of myopia, by increasing the radius of curvature of the central cornea while leaving the peripheral curvature unchanged, has demonstrated the ability to reduce or halt the progression of myopia. The mechanism is understood to be the placement of the peripheral image field in front of the retina while the central image field is accurately focused on the retina.

Emerging myopia or incipient myopia is characterized as a stage in refractive error development when the eye is shifting from greater hyperopia to less hyperopia or when the eye is shifting from emmetropia to myopia. Longitudinal studies of human populations reveal the onset of emerging myopia as early as the age of six. Corneal refractive therapy or overnight corneal reshaping is effective for the temporary reduction of myopia and appears to be effective in regulating the axial length growth of eyes treated for myopia. The current lens designs are intended to increase the radius of curvature of the central cornea and are not indicated for treatment of emerging myopia where the desired treatment would not increase the radius of curvature of the central cornea, for example, where there is a need to decrease the radius of curvature of the mid peripheral cornea.

The prior art teaches the methods of reshaping the central cornea to correct refractive error. For the treatment of myopia, the central corneal radius is increased by way of applying a lens having a central radius of curvature longer than the pre-treated central corneal radius. In the prior art, the mid peripheral cornea is found to remain substantially unchanged during treatment.

For example, prior art contact lens corneal reshaping for the temporary reduction of refractive error utilizes lenses wherein the central zone of the lens is referred to and recognized as the treatment zone. The intention of the prior art is to change the shape of the central cornea in an amount required to reduce the refractive error to a negligible amplitude. If, for example, the pre-treatment refractive error is −3.00 D, or three diopters of myopia, the treatment goal would be to increase the radius of curvature of the central cornea the required length to reduce the power of the cornea by 3.00 diopters. There is no known practice or teaching that suggests any intention to reshape the mid peripheral cornea.

SUMMARY OF THE INVENTION

In accordance with exemplary embodiments of the present invention, an eye is presented with a therapeutic optical structure that focuses the peripheral image field in at least one semi meridian in front of the mid peripheral retina. In general, the therapeutic optical structure places the peripheral image field with reference to the retina in the direction and amplitude that growth is needed in order that the emerging myopia would be regulated. In accordance with exemplary embodiments of the present invention, an eye is presented with a therapeutic optical structure that further produces a central retinal image that is focused on the central retina in at least one meridian so as to not substantially reshape the central cornea.

Exemplary therapeutic optical structures can be achieved by way of corneal reshaping or by way of a contact lens, or other refractive correction system or method, wherein the peripheral image field is relatively defocused, and in some embodiments, wherein the central image is focused in at least one meridian.

In the case of corneal reshaping, an exemplary treatment may produce a peripheral corneal shape that would focus the peripheral image field in front of the peripheral retina. In some embodiments, an exemplary treatment would produce a central corneal geometry that would render or keep the eye emmetropic or hyperopic.

In exemplary embodiments comprising a contact lens not intended for corneal reshaping yet intended for the regulation of emerging myopia, a central zone may be selected to have a power equal to or not equal to the refractive error of the eye for the purpose of focusing the image relative to the central retina. An annular zone surrounding the central zone may be configured to produce an off axis retinal defocus such that the peripheral image field is focused in front of the retina for the purpose of regulating the growth of the eye in the respective semi meridian.

BRIEF DESCRIPTION OF THE DRAWINGS

The exemplary embodiments of the present invention will be described in conjunction with the appended drawing figures in which like numerals denote like elements and.

DETAILED DESCRIPTION

The present invention relates to systems and methods for the regulation of emerging myopia. One skilled in the art will appreciate that various aspects of the invention may be realized by any number of materials or methods configured to perform the intended functions. For example, other materials or methods may be incorporated herein to perform the intended functions. It should also be noted that the drawing figures referred to herein are not all drawn to scale, but may be exaggerated to illustrate various aspects of the invention, and in that regard, the drawing figures should not be construed as limiting.

Exemplary embodiments of the present invention may be used to prevent or otherwise regulate emerging myopia or incipient myopia, for example, in children. However, one skilled in the art will appreciate that this invention may apply to persons of varying ages. This invention will be especially useful in connection with patients not yet experiencing myopia.

Figure 1:
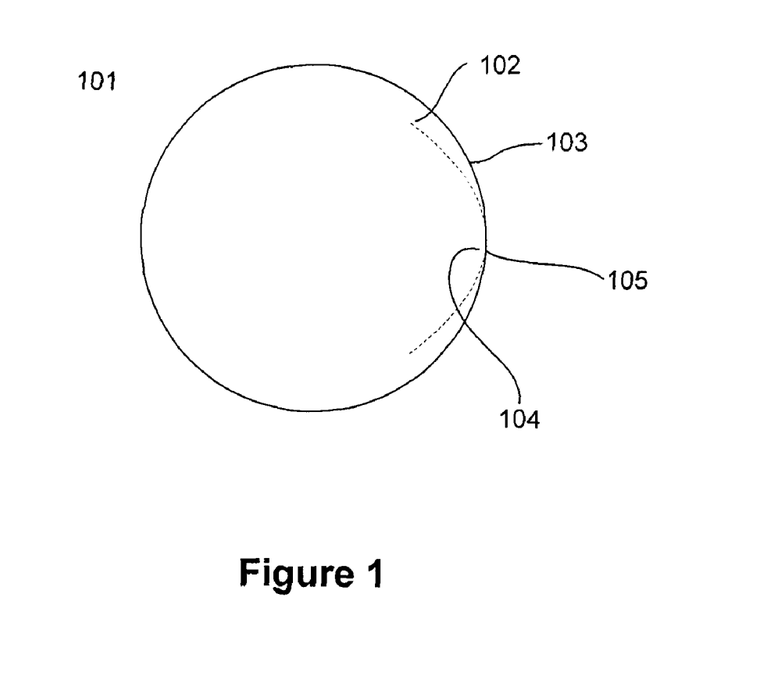
FIG. 1 illustrates a therapeutic image field with reference to the retina in accordance with an exemplary embodiment of the present invention.

In accordance with exemplary embodiments of the present invention, and with reference to FIG. 1, an eye 101 is presented with a therapeutic optical structure that focuses the peripheral image field 102 in at least one meridian in front of the mid peripheral retina 103. In general, the therapeutic optical structure places the peripheral image field with reference to the retina in the direction that growth regulation is needed in order that the emerging myopia would be regulated. In accordance with exemplary embodiments of the present invention, eye 101 is presented with a therapeutic optical structure that further produces a central retinal image 104 that is focused on the central retina 105 in at least one meridian so as to not substantially reshape the central cornea.

In exemplary embodiments, the therapeutic optical structure is configured for direct or indirect contact with ocular tissue of a human or other mammal. For example, in accordance with one aspect of an exemplary embodiment, the therapeutic optical structure is configured to rest upon the cornea, and in some cases also the sclera, of the eye, similar to a conventional soft, hybrid bimodulus, or rigid contact lens. In other embodiments, however, the therapeutic optical structure is configured for placement within ocular tissue, for example, as an intracorneal or intraocular implant.

In accordance with exemplary embodiments, the therapeutic optical structure is comprised of one or more gas permeable, or otherwise biocompatible, materials. For instance, the therapeutic optical structure may be comprised of one or more of fluorosilicon acrylate, silicon acrylate, polymethylmethacrylate, a silicon hydrogel, or another suitable material. It is also contemplated that different portions of a given therapeutic optical structure may be comprised of the same or different materials.

In general, therapeutic optical structure should be broadly construed such that any structure or method by which the central retinal image may be, but is not necessarily, focused in all meridians, and at least one semi-meridian of the peripheral image field is not focused on the retina, falls within the scope thereof. In that regard, various forms of laser surgery known in the art are contemplated as additional therapeutic optical structures within the spirit and scope of the present invention.

Exemplary therapeutic optical structures can be achieved by way of corneal reshaping or by way of a contact lens, or other refractive correction system or method, wherein the peripheral image field is relatively defocused, and in some embodiments, wherein the central image is focused in at least one meridian.

Reshaping Lens

Figure 2:
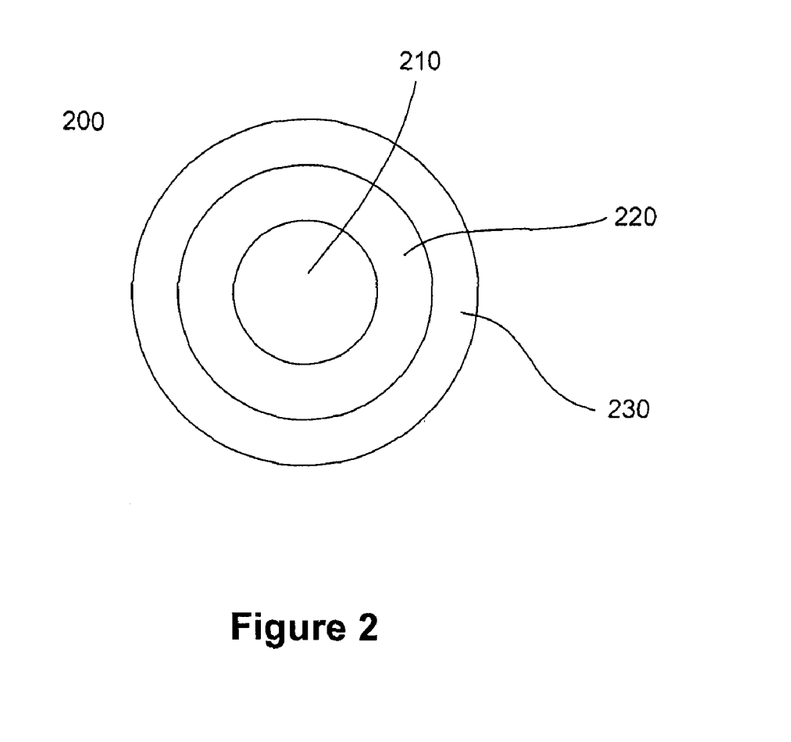
FIG. 2 illustrates a contact lens for corneal reshaping in accordance with an exemplary embodiment of the present invention.

In accordance with exemplary embodiments, and with reference to FIG. 2, a contact lens 200 for corneal reshaping comprises a central zone 210, an annular zone 220, and a peripheral zone 230.

In exemplary corneal reshaping embodiments, central zone 210 is the alignment zone, annular zone 220 outside central zone 210 is the treatment zone, and peripheral zone 230 outside annular zone 220 is the landing or conforming zone. For example, in accordance with one embodiment, annular zone 220 vaults the mid peripheral cornea in at least one meridian, while central zone 210 and peripheral zone 230 are in contact with the cornea in the same meridian. In exemplary corneal reshaping embodiments, the central cornea is substantially unchanged while the mid peripheral cornea is reshaped to thereby increase in power relative to off axis incident light.

Central Zone

In exemplary embodiments, the central zone has an apical radius that is substantially the same as the pre-treatment central corneal apical radius. In exemplary embodiments, the central zone of the lens has a higher eccentricity than the cornea being treated. As a result, in exemplary embodiments the central zone of the lens is in alignment centrally and gains clearance from the cornea at its periphery and junction with the annular zone.

In exemplary embodiments, the central zone of the lens is structurally or materially configured to provide at least one of rotational stability, alignment and/or centration, as will be discussed in greater detail below.

In accordance with exemplary embodiments, the central zone is configured to focus the central retinal image in all meridians, while in other exemplary embodiments, the central zone is configured to defocus the central retinal image in one or more meridians. In accordance with exemplary embodiments, the central zone is selected to have a power equal to or not equal to the refractive error of the eye for the purpose of focusing the image relative to the central retina.

In accordance with exemplary embodiments, the central zone is generally concentric with and comprises the axial center of the therapeutic optical structure. In some embodiments, the central zone has a diameter of from about 0.1 mm to about 14 mm and more preferably from about 3 mm to about 7 mm.

In exemplary embodiments, the central zone is configured to have a spherical geometry, while in others, it may have an aspherical, toric, multifocal or rotationally non-symmetrical geometry, depending on the refractive error to be regulated and/or the ocular tissue to be fitted. Such measurements may be obtained for example, using keratometry, corneal topography, optical coherence tomography, Scheimpflug imaging, or other conventional biometric instrumentation.

Annular Zone

In exemplary embodiments, a contact lens for corneal reshaping comprises one or more annular zones, for example, configured to reshape an aspect of the mid peripheral cornea such that the aspect thereby focuses the peripheral image field in at least one semi meridian in front of the mid peripheral retina. In exemplary embodiments, an annular zone has a width substantially similar to that of the underlying mid peripheral cornea. In exemplary embodiments, the width of the annular zone is from about 0.25 mm to about 4 mm, or more preferably from about 0.75 mm to about 2 mm, or most preferably about 1.25 mm. Moreover, the annular zone width may have a variable width circumferentially.

In exemplary embodiments, an annular zone vaults the mid peripheral cornea by having a radius that is shorter than that of the underlying mid peripheral cornea. One skilled in the art will appreciate that various other approaches may be used such that an annular zone vaults the mid peripheral cornea. The sagittal profile of an annular zone that vaults the mid peripheral cornea may be spherical, aspherical, defined by a polynomial, uncurved and defined by an angle or may be defined by spline mathematics in the same semi meridian. In exemplary embodiments, an annular zone may be described as a sigmoid. In general, the geometry of an annular zone can be modulated to become the mould for the transfer of material to the zone, as will be discussed herein.

In exemplary embodiments, the center of curvature of an annular zone is off axis from the apical radius. In this manner, the annular zone remains anterior to the cornea throughout its peripheral extension and it terminates at the peripheral zone anterior to the cornea by an amount approximately equal to its most medial aspect.

One skilled in the art will appreciate that numerous methods may be used to define the center of curvature of an annular zone off axis from the apical radius, for example, those disclosed in U.S. Pat. No. 7,216,974, entitled "Contact Lens And Methods of Manufacture," which is incorporated herein by reference in its entirety.

In exemplary embodiments, corneal reshaping varies between semi-meridians adjacent, orthogonal, and/or alternate to one another. In other words, an annular zone may be rotationally asymmetric to thereby influence local globe growth and shape of the globe (e.g., axial, equatorial, mid peripheral and/or far peripheral) in a rotationally asymmetric manner.

Peripheral Zone

In exemplary embodiments, a contact lens for corneal reshaping comprises a peripheral zone. In exemplary embodiments, the peripheral zone has a width of from about 0.05 mm to about 7 mm and more preferably from about 1.25 mm to about 5 mm.

In exemplary embodiments, the peripheral zone is uncurved and defined by an angle such that it is not in contact with the peripheral cornea at its most medial aspect or peripheral aspect, but is in contact with the peripheral cornea at a point of tangency on the peripheral cornea.

While it is contemplated that the peripheral zone in some embodiments could be curved and/or defined by a polynomial, in exemplary embodiments, the peripheral zone is uncurved and defined by an angle. The angle may be defined in any number of ways. For example, in one embodiment, the angle is defined between a chord perpendicular to the central axis of the lens that passes through the junction between an annular zone and the peripheral zone and a line from the apex to the point of tangency on the cornea. In exemplary embodiments, the point of tangency is approximately midway between its most medial aspect and most peripheral aspect.

One skilled in the art will appreciate that numerous methods may be used to define the angle, for example, those disclosed in co-pending U.S. patent application Ser. No. 12/428,424, entitled "Scleral Contact Lens and Methods for Making and Using the Same," which is incorporated herein by reference in its entirety.

Reshaping Mechanism

Figure 3A:
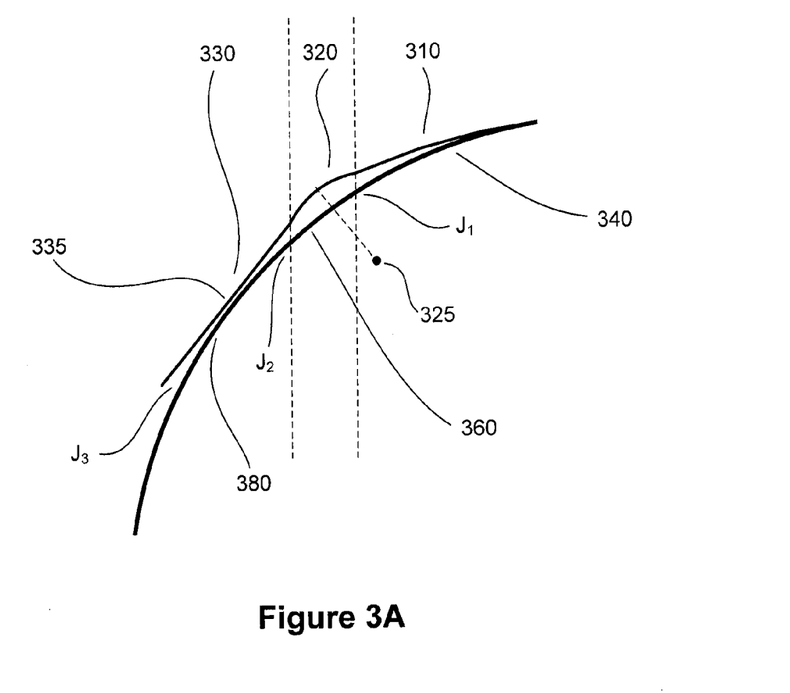
FIGS. 3A-3B illustrate the spatial relationship between the cornea and contact lenses for corneal reshaping in accordance with exemplary embodiments of the present invention.

Turning back to the figures and with reference to FIG. 3A, a contact lens for corneal reshaping in accordance with various embodiment of the present invention comprises a central zone 310, an annular zone 320, and a peripheral zone 330, the lens being configured to rest upon the cornea. As noted above, while a single annular zone is described for simplicity, a plurality of annular zones is contemplated.

In exemplary embodiments, central zone 310 aligns the central cornea 340 in a manner that is intended to leave the curvature of central corneal 340 and its power substantially unchanged. In exemplary embodiments, the higher eccentricity of central zone 310 than central cornea 340 is intended to create a toroid of clearance between the central zone 310 and central cornea 340 just medial to annular zone 320 at point $J_1$. This toroid of clearance allows for the commencement of an increase in corneal thickness just medial to annular zone 320 and facilitates a transfer of epithelial cells and intracellular and intrastromal fluids into annular zone 320 as a response to the compression force of the lens on the eye during closed eye wearing and due to lid force pushing on aligned central zone 310 and on peripheral zone 330.

In exemplary embodiments, the center of curvature 325 of annular zone 320 is off axis from the apical radius. In this manner, annular zone 320 remains anterior to the cornea throughout its peripheral extension and it terminates at peripheral zone 330 anterior to the cornea at point $J_2$ by an amount approximately equal to its most medial aspect at point $J_1$.

In exemplary embodiments, if annular zone 320 has a conventional reverse geometry design having a shorter radius of curvature than central zone 310 but being coaxial with central zone 310, the peripheral aspect of annular zone 320 would most often be deeper than the cornea thereby causing the medial aspect of peripheral zone 330 to impinge or bear heavily on the cornea at or near point $J_2$. Moreover, central zone 310 would be elevated anterior to the cornea. As a result, there would be no compression force in central zone 310 to cause a movement of tissue into the region underlying annular zone 320. The utility of the off axis annular zone 320 solves a fundamental problem that would often be present if annular zone 320 were on the axis of central zone 310.

In accordance with exemplary embodiments, the shape of the posterior surface of annular zone 320 and the continued clearance anterior to the mid peripheral cornea 360 provide a void into which cells and fluids can pass. In addition, a toroid of clearance at the most medial aspect of peripheral zone 330 at point $J_2$ allows for an increase in corneal thickness just peripheral to annular zone 320 and facilitates a transfer of epithelial cells and intracellular and intrastromal fluids into the cornea posterior to annular zone 320 as a response to the compression force of the lens on the eye during closed eye wearing and due to lid force pushing on aligned central zone 310 and on peripheral zone 330.

As noted earlier, in exemplary embodiments, peripheral zone 330 is uncurved and defined by an angle such that it is not in contact with peripheral cornea 380 at its most medial aspect $J_2$ or peripheral aspect $J_3$, but is in contact with peripheral cornea 380 at a point of tangency 335 on peripheral cornea 380.

Figure 3B:
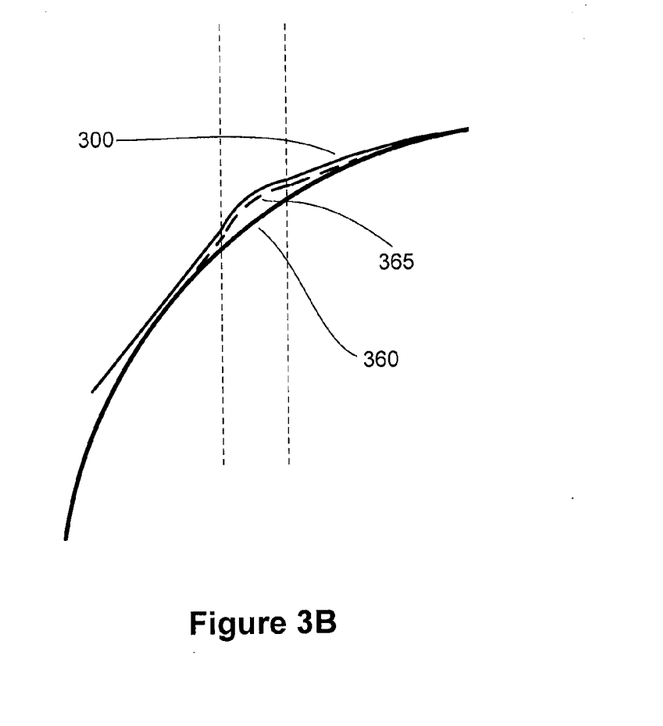

With reference to FIG. 3B, when applied to the eye and worn in a program of corneal reshaping (e.g., overnight corneal reshaping), the lens 300 of this invention in exemplary embodiments would cause mid peripheral cornea 360 in the same meridian to increase in optical power (e.g., decrease the radius of curvature to create an off axis shorter focal length for the optically corresponding mid peripheral retina) with regard to an off axis peripheral focus from about 5 to about 80 degrees, or more preferably from about 20 to about 50 degrees, from the fovea of the eye, as illustrated by the dash line at reference numeral 365 in FIG. 3B. The peripheral defocus in exemplary embodiments is intended to be in front of the retina in at least one semi meridian for the purpose of regulating the growth of the eye in the respective semi meridian. In exemplary embodiments, the central cornea in at least one meridian remains unchanged. In exemplary embodiments, post treatment, the cornea maintains substantially the same keratometric curvature and power with an increase in eccentricity followed by a substantial increase in mid peripheral power in an off axis annular zone.

Method of Fitting Reshaping Lens

Figure 4:
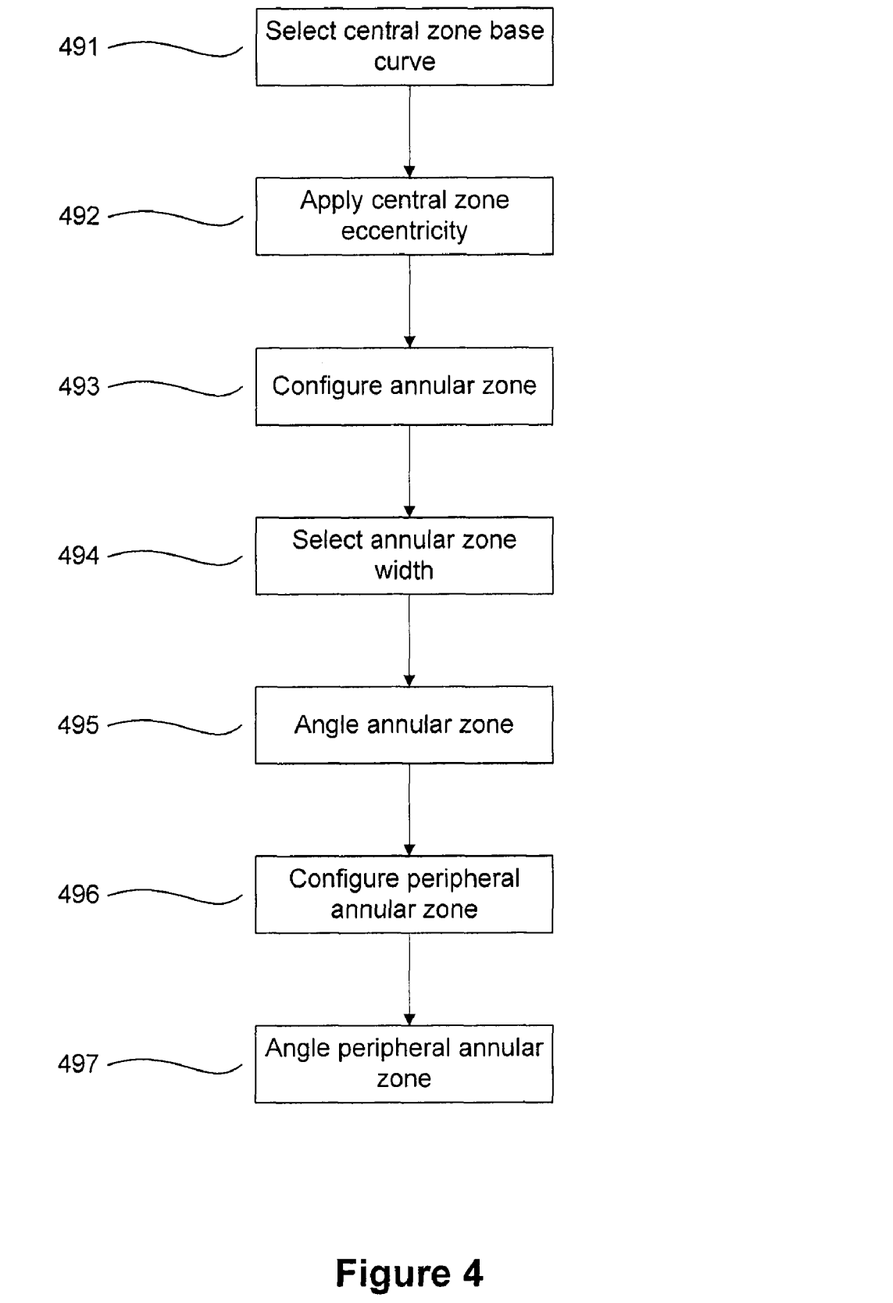
FIG. 4 illustrates a flow diagram of an exemplary method of fitting a contact lens for corneal reshaping.

With reference to FIG. 4, an exemplary method of fitting a contact lens for corneal reshaping 490 will now be described, which one skilled in the art will appreciate need not necessarily be performed in the order described.

In step 491, a base curve for the central zone is selected that is substantially similar to the central corneal curvature. In step 492, the eccentricity of the cornea is measured using corneal topography or the like, and an eccentricity is applied to the central zone that is greater than the measured eccentricity of the cornea in an effort to create a clearance of about 30 microns at a chord of approximately 6 mm.

In step 493, the lens is configured to have an off axis annular zone that is from about 0.1 mm to about 1.0 mm shorter, or more preferably from about 0.2 mm to about 0.8 mm shorter, or most preferably about 0.4 mm shorter in radius than the pre-treatment corneal radius of curvature. In step 494, the width of the annular zone is selected. In exemplary embodiments, the width of the annular zone is from about 0.25 mm to about 4 mm, or more preferably from about 0.75 mm to about 2 mm, or most preferably about 1.25 mm. One skilled in the art will appreciate that numerous geometric configurations provide alternate methods to create equivalent annular zone clearance from the mid peripheral cornea; for example, by way of using a shape defined by a polynomial or spline mathematics or by use of a radius that is equal to or longer than the central radius of curvature having its center of curvature off axis from the central zone. In step 495, the annular zone is angled to create a clearance at the termination of the zone of about 30 microns. Once again, corneal topography or the like may be used to measure the elevation of the cornea at the respective chord diameter of the annular zone.

In step 496, a peripheral zone is configured that is uncurved and defined by an angle. In step 497, an angle is selected that provides a point of tangency on the peripheral cornea about midway from the junction with the annular zone and the edge of the lens such that the lens demonstrates a clearance of about 30 microns at the medial aspect of the zone just peripheral to $J_2$.

Non Reshaping Lens

Figure 5:
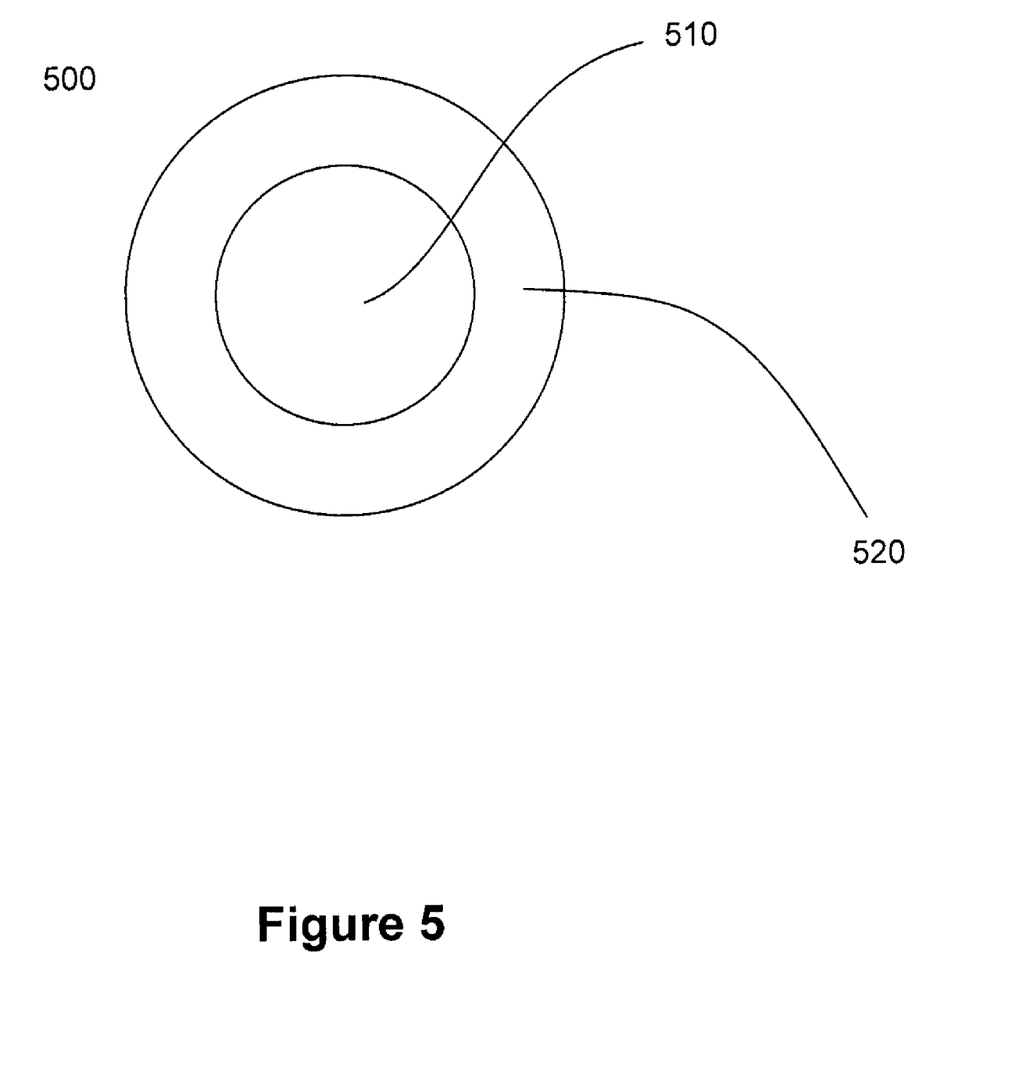
FIG. 5 illustrates a contact lens not intended for corneal reshaping yet intended for the regulation of emerging myopia in accordance with an exemplary embodiment of the present invention.

In accordance with exemplary embodiments, and with reference to FIG. 5, a contact lens 500 not intended for corneal reshaping yet intended for the regulation of emerging myopia comprises a central zone 510 and an annular zone 520.

Central Zone

In exemplary embodiments, the central zone has an apical radius that is substantially the same as the pre-treatment central corneal apical radius.

In exemplary embodiments, the central zone of the lens is structurally or materially configured to provide at least one of rotational stability, alignment and/or centration, as will be discussed in greater detail below.

In accordance with exemplary embodiments, the central zone is configured to focus the central retinal image in all meridians, while in other exemplary embodiments, the central zone is configured to defocus the central retinal image in one or more semi-meridians. In accordance with exemplary embodiments, the central zone is selected to have a power equal to or not equal to the refractive error of the eye for the purpose of focusing the image relative to the central retina.

In accordance with exemplary embodiments, the central zone is generally concentric with and comprises the axial center of the therapeutic optical structure. In some embodiments, the central zone has a diameter of from about 0.1 mm to about 14 mm and more preferably from about 3 mm to about 7 mm.

In exemplary embodiments, the central zone is configured to have a spherical geometry, while in others, it may have an aspherical, toric, multifocal or rotationally non-symmetrical geometry, depending on the refractive error to be regulated and/or the ocular tissue to be fitted. Such measurements may be obtained for example, using keratometry, corneal topography, optical coherence tomography, Scheimpflug imaging, or other conventional biometric instrumentation.

Annular Zone

In exemplary embodiments, a contact lens not intended for corneal reshaping yet intended for the regulation of emerging myopia comprises one or more annular zones, for example, comprising optics to focus the peripheral image field in at least one semi-meridian in front of the mid peripheral retina. In exemplary embodiments, an annular zone has a width substantially similar to that of the underlying mid peripheral cornea. In exemplary embodiments, the width of the annular zone is from about 0.25 mm to about 4 mm, or more preferably from about 0.75 mm to about 2 mm, or most preferably about 1.25 mm. Moreover, the annular zone width may have a variable width circumferentially.

In exemplary embodiments, annular zone optics vary between semi-meridians adjacent, orthogonal, and/or alternate to one another. In other words, an annular zone may be rotationally asymmetric to thereby influence local globe growth and shape of the globe (e.g., axial, equatorial, mid peripheral and/or far peripheral) in a rotationally asymmetric manner. Additionally, annular zone optics may vary radially along a single semi-meridian.

In general, one skilled in the art will appreciate that numerous approaches may be taken to accomplish select mid peripheral retinal focus, all of which are contemplated herein. For example, select mid peripheral retinal focus may be achieved with refractive, birefringent, or diffractive optics.

In exemplary embodiments, select mid peripheral retinal focus is achieved with an annular zone having a refractive power different relative to the central zone such that all or a portion of off-axis light rays along a semi-meridian focus in front of or behind off-axis light rays along another semi-meridian, with reference to the retina.

In other embodiments, select mid peripheral retinal focus is achieved with an annular zone comprised of a birefringent material having properties selected to cause all or a portion of off-axis light rays along a semi-meridian to be focused in front of or behind off-axis light rays along another semi-meridian, with reference to the retina, for example, in a manner similar to that described in co-pending U.S. patent application Ser. No. 12/110,999, entitled "System and Method to Treat and Prevent Loss of Visual Acuity," which is incorporated herein by reference in its entirety.

In other embodiments, select mid peripheral retinal focus is achieved with diffractive optics. More particularly, in exemplary embodiments, diffractive optics are used to focus all or a portion of peripheral light rays along a semi-meridian in front of or behind peripheral light rays along another semi-meridian, with reference to the retina.

Rotational Stability, Alignment and/or Centration

Exemplary therapeutic optical structures in accordance with the present invention may be used in connection with one or more structural or material design elements configured to provide rotational stability, alignment and/or centration.

For example, with application to exemplary structures configured to rest upon the cornea, some embodiments comprise one or more of prism ballasting, double slab off, and anterior thickness variations to assist with rotational stability, alignment and/or centration. In some embodiments, rotational stability, alignment and/or centration is improved by spatially matching the posterior structure surface with one or more corneal or scleral topographical variations, for example, in a manner similar to that described in co-pending U.S. patent application Ser. No. 12/413,319, entitled "Contact Lens with Meridional Sagittal Variation and Methods for Making and Using the Same," which is incorporated herein by reference in its entirety.

Similarly, with application to exemplary structures configured for placement within ocular tissue, (in addition to, or in substitution of, those described above) some embodiments comprise one or more of corneal pockets, adhesives, laser sealing, and sutures to assist with rotational stability, alignment and/or centration.

Persons skilled in the art will appreciate many methods or structural or material design elements configured to give rotational stability, alignment and/or centration to therapeutic optical structures of the present invention, all of which fall within the spirit and scope of the invention.

The foregoing disclosure is illustrative of the present invention and is not to be construed as limiting the invention. Although one or more embodiments of the invention have been described, persons skilled in the art will readily appreciate that numerous modifications could be made without departing from the spirit and scope of the present invention. As such, it should be understood that all such modifications are intended to be included within the scope of the invention.

We claim:

1. A therapeutic optical structure for regulating emerging myopia comprising a central zone, an annular zone, and a peripheral zone,
    wherein said central zone has a higher eccentricity than the underlying cornea;
    wherein a peripheral aspect of said central zone is configured to not touch the cornea;
    wherein the sagittal profile of said annular zone is one of spherical, aspherical, defined by a polynomial, uncurved and defined by an angle, or defined by spline mathematic;
    wherein a peripheral aspect and a medial aspect of said annular zone are configured to not touch the cornea;
    wherein said annular zone is configured to reshape an aspect of the mid peripheral cornea such that said aspect thereby focuses a peripheral image field in at least one semi-meridian in front of the mid peripheral retina;
    wherein a peripheral aspect and a medial aspect of said peripheral zone are configured to not touch the cornea; and
    wherein said peripheral zone is in contact with the peripheral cornea between the peripheral aspect and the medial aspect of said peripheral zone.

2. A therapeutic optical structure according to claim 1, wherein said annular zone is not in contact with the cornea between said peripheral aspect and said medial aspect of said annular zone creating a region into which said aspect of the mid peripheral cornea is reshaped.

3. A therapeutic optical structure according to claim 1, wherein the central zone is configured to provide at least one of rotational stability, centration and alignment.

4. A therapeutic optical structure according to claim 1, wherein the annular zone is configured to have a center of curvature that is off axis from the radius of curvature of said central zone.

5. A therapeutic optical structure according to claim 1, wherein the peripheral zone is configured to be curved and controlled by an angle.

6. A therapeutic optical structure according to claim 5, wherein the curve of the peripheral zone controlled by an angle is convex to the eye.

7. A therapeutic optical structure according to claim 5, wherein the curve of the peripheral zone controlled by an angle is aspheric.

* * * * *